United States Patent [19]
Huffman

[11] Patent Number: 5,615,691
[45] Date of Patent: Apr. 1, 1997

[54] SHIELDING DEVICE FOR THE PERINEAL AREA

[76] Inventor: Mary Huffman, 168 24th St. North, Jacksonville Beach, Fla. 32250

[21] Appl. No.: 373,646

[22] Filed: Jan. 17, 1995

[51] Int. Cl.$^6$ ............ A61F 13/00; A61F 13/15
[52] U.S. Cl. ............ 128/891; 128/888; 604/393; 604/385.1
[58] Field of Search ............ 604/355, 358, 604/359, 385.1, 387, 402, 393, 400; 128/888, 889, 891, 846

[56] References Cited

U.S. PATENT DOCUMENTS

| | | | |
|---|---|---|---|
| 695,270 | 3/1902 | Beringer | 128/888 |
| 2,831,486 | 4/1958 | Sanders | 128/891 |
| 4,023,569 | 5/1977 | Warnecke et al. | 128/888 |
| 4,134,399 | 1/1979 | Halderson | 128/888 |
| 4,641,641 | 2/1987 | Strock | 128/846 |
| 4,667,666 | 5/1987 | Fryslie | 128/888 |
| 4,880,417 | 11/1989 | Yabrov et al. | 604/355 |
| 5,020,547 | 6/1991 | Strock | 128/891 |
| 5,154,715 | 10/1992 | Van Iten | 604/387 |
| 5,174,307 | 12/1992 | Thompson | 128/891 |

FOREIGN PATENT DOCUMENTS

| | | | |
|---|---|---|---|
| 1146313 | 11/1957 | France | 128/888 |
| 1291136 | 3/1962 | France | 128/888 |

*Primary Examiner*—Mark O. Polutta
*Attorney, Agent, or Firm*—Thomas C. Saitta

[57] ABSTRACT

A non-contacting shield for use in the perineal area, comprising a main body maintained a distance from the perineal area by two lateral panels which fold generally perpendicularly relative to the main body. The lateral panels, preferably expanded or padded along the outer portion, are positioned adjacent the inner thighs and occupy the pockets formed by the juncture of the thighs and pelvis. The lateral panels are arcuate and the main body is composed of a flexible material to allow it to conform to the shape of the perineal area.

12 Claims, 1 Drawing Sheet

SHIELDING DEVICE FOR THE PERINEAL AREA

BACKGROUND OF THE INVENTION

The invention relates generally to the field of shields or dressings designed for use on the human body, and more particularly to such shields adapted to create an area of separation between the skin and clothing, other parts of the body, absorbent pads, etc. Even more particularly, the invention relates to shields for use in the female perineal area, inclusive of the vulva, perineum and anus, which are specially adapted to provide comfort or promote healing.

In the treatment of many injuries, skin disorders, infections, lesions, hemorrhoids, surgical incisions, etc., it is usually preferred that the area be somewhat exposed to air flow and that contact with clothing, other body parts, or external objects be prevented. Reducing contact prevents loss of medication and irritation of the area being treated, thereby accelerating the healing process and increasing comfort. It is especially difficult to accomplish these goals where treatment of injuries, lesions, infections, hemorrhoids, disorders or incisions in the female perineal area is necessary—the female perineal area being herein defined as the area generally located between the thighs and encompassing the vulva, perineum and anus. Clothing such as underwear or pants will directly contact or rub against the perineal area. Typical dressings for the area, such as panty liners or sanitary napkins, do not alleviate the contact, ventilation and irritation problems as they are designed to be in direct contact with the skin, and such dressings can even be detrimental as they will absorb medication away from the treatment area. Because they are in direct contact, ventilation and air flow is restricted and frequent changing of the liners or napkins is required to maintain a clean environment due to increased perspiration and possible bacteria growth.

It is an object of this invention to provide a shield for the perineal area which provides an isolation and non-contact zone between the perineal area and clothing or other skin, whereby medication will not be absorbed from the treatment area, ventilation and air flow will be present to promote rapid healing and to limit perspiration and bacteria growth, and irritation of the treatment area will be prevented. It is a further object to provide such a device which is comfortable for the wearer. It is a further object to provide such a device adapted to receive absorbent pads if required, yet still maintain the non-contact area above the perineal area.

SUMMARY OF THE INVENTION

The device is a shield or dressing for use in the perineal area which is adapted to provide an isolation and non-contact area between the perineal area (the vulva, perineum and anus) and clothing, skin or other objects to promote better healing of injuries, disorders, infections, lesions, incisions or the like by improving ventilation, preventing the absorption of medication away from the treatment area and preventing irritation from friction or contact. In general, the device comprises a relatively thin, generally rectangular or bi-concave main body member adapted to be situated with its longitudinal axis extending from the vulva region to the anal region, with a length sufficient to cover the vulva and anus and with a width conducive to comfortable positioning between the legs of the wearer. A lateral panel member is connected along each longitudinal edge of the main body at a fold line, whereby each lateral panel member can be folded approximately 90 degrees relative to the main body member. The main body and the lateral panels are composed of a relatively rigid yet flexible material, such that each can adapt to the contours of the perineal area. In order to accomplish this, the outer edge of each lateral panel is arcuate or concave, each free end of the lateral panels are curved or arcuate, and the fold line juncture between each lateral panel and the main body is short enough to allow the main body to flex longitudinally to be positioned against the curved ends of the lateral panels. The outer portion of each lateral panel is preferably expanded or padded for comfort, to increase its resistance to compression or folding, and to provide means to maintain the lateral panels in angular relation to the main body to separate the main body from the perineal area when the device is worn, as the expanded portions will be held in place in the two generally linear pockets formed at the juncture between the thighs and the labia. The main body may be perforated for ventilation and an adhesive strip may be added to adhere the outer surface to clothing. It is preferred that the device be disposable and sterile.

DETAILED DESCRIPTION OF THE INVENTION

With reference to the drawings, the preferred embodiment and best mode of the invention will now be described. The invention comprises in general a shield or dressing device for use in the perineal area, herein defined to include the vulva region, the perineum and the anal region, which is adapted to provide an isolation and non-contact area between the perineal area and clothing, skin or other objects to promote better healing of injuries, disorders, infections, lesions, hemorrhoids, incisions or the like by improving ventilation, preventing the absorption of medication away from the treatment area and preventing irritation from friction or contact. It is preferably sterile and disposable, and may be composed of single or multiple layers of materials having suitable rigidity, flexibility and strength, such as paper, cardboard, foam, plastics, wovens or reinforced non-wovens.

Figure 1:
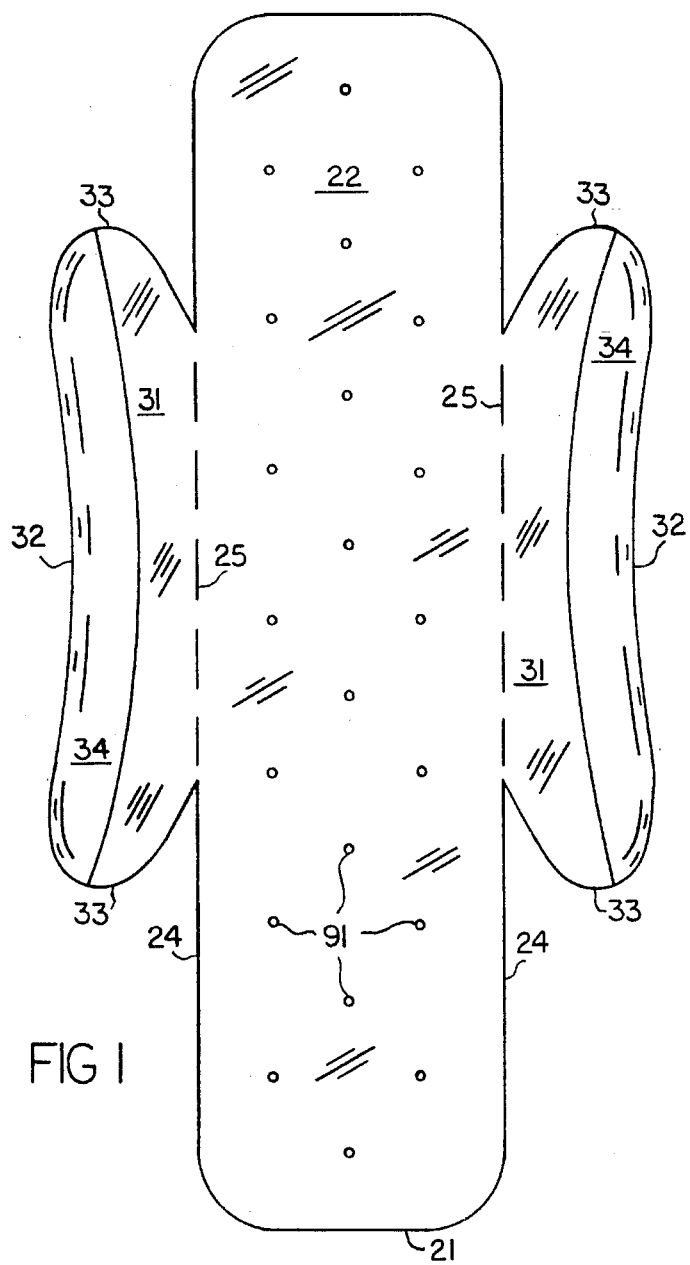
FIG. 1 is a top view of the invention in the unfolded configuration.
Figure 2:
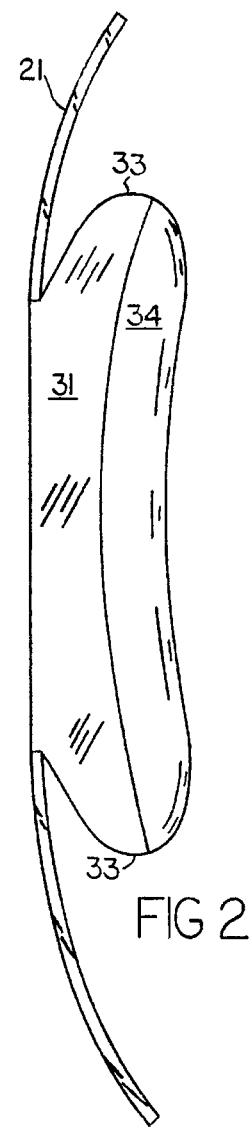
FIG. 2 is a side view of the invention in the folded or in-use configuration.
Figure 3:
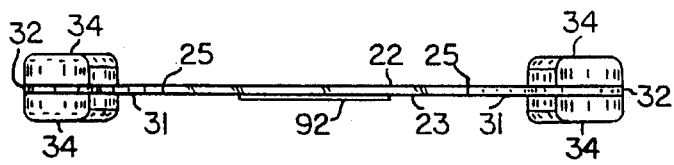
FIG. 3 is an end view of the invention in the unfolded configuration.

Referring now to FIGS. 1 and 3, the device is shown to comprise a main body 21 adjoined by two lateral panels or flaps 31. The main body 21 is generally rectangular in overall configuration as shown with two opposing longitudinal edges 24, an inner or top surface 22 and an outer or bottom surface 23. The main body 21 is preferably sized longer in the longitudinal direction than in the lateral direction, such as for example approximately eight inches long by two inches wide, and is preferably relatively thin, such as for example approximately one eighth inches thick. Other general shapes for the main body 21 are also possible, such as a bi-concave configuration where the main body 21 is narrower in the middle than at the ends. The inner surface 22 is the surface facing the perineal area when worn and will be flexed in a concave manner as shown in FIG. 2. The outer surface 23 is the surface facing the clothing or away from the perineal area when worn and will be flexed in a convex manner. The main body 21 may be absorbent or non-absorbent. It is preferred that the inner surface 22 and outer surface 23 be generally smooth. The main body 21 is preferably composed of a semi-rigid material such that it is flexible longitudinally to allow the main body to curve as shown in FIG. 2. This allows the main body 21 to better conform to the shape of the perineal area, such that it is more comfortable for the user, especially when clothes are worn. The main body 21 must have sufficient rigidity however to prevent folding or compression into the separation area between the upper surface 22 and the perineal area.

Figure 4:
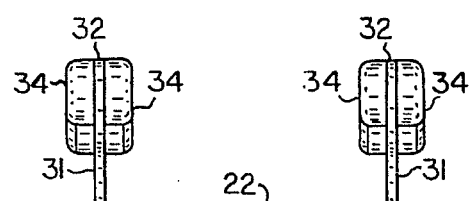
FIG. 4 is an end view of the invention in the folded configuration.

Two opposing lateral panels or flaps 31 are adjoined to the longitudinal edges 24 of the main body 21 along junctions or folds 25. Each lateral panel 31 comprises an outer edge 32, two opposing free ends 33 and an expanded portion 34. The lateral panels 31 are preferably composed of material similar to that of the main body 21, and must have sufficient rigidity to resist folding or compression, although they should have some degree of flexibility for comfort. The lateral panels 31 are adapted to fold along folds 25 so as to be generally perpendicular to the main body 21 when in use, as seen in FIGS. 2 and 4. Each fold 25 occupies a short and generally central portion of the longitudinal edge 24 of main body 21, such that the ends of main body 21 remain free. For example, lateral panels 31 approximately four inches in length are suitable for use with an eight inch long main body 21. Preferably the lateral panels 31 are not centered on the longitudinal midpoint of the main body 21, with the result that the rearward portion of the main body 21 for covering the anal region will be longer than the forward portion for covering the vulva region. When folded into the generally perpendicular configuration, the lateral panels 31 are positioned adjacent the inner thighs of the wearer. The lateral panels 31 are approximately one inch in height, and thus lift the main body 21 away from the perineal area when folded, creating an isolation or non-contact zone of one inch between the upper surface 22 of main body 21 and the perineal area.

Preferably the outer edge 32 of each lateral panel 31 is curved or arcuate for better conformation of the overall device to the perineal area. Likewise, each panel end 33 is preferably curved to create a gap of increasing dimension from the fold 25 to each panel end 33, such that the general overall configuration of each lateral panel 31 is arcuate. The combination of the short fold 25 and the curved panel ends 33 allows the main body to adopt a longitudinally curved shape when worn, as seen in FIGS. 2 and 4, while maintaining sufficient length in the lateral panels 31 to create a longitudinally extended separation zone between the inner surface 22 of main body 21 and the perineal area. For comfort, to increase the strength of the lateral panels 31, and to provide a means to secure the lateral panels 31 in place and retain them at an angle to the main body 21, it is preferred that the lateral panels further comprise an expanded or padded portion 34 extending some distance from each outer edge 32 toward the fold 25, as shown in FIGS. 1 and 3. This expanded portion 34 creates a more comfortable contact surface between the lateral panels 31 and the wearer, as well as adding to tile structural integrity of the device against folding or compression during use. When worn the expanded portion 34 of each lateral panel 31 fits into as is held in place by the pocket or crease formed at tile inner juncture of the thigh and pelvis. The labia further define this pocket on either side, such that the thinner region of the lateral panel 31 is pressed between the thigh and labia to further maintain the lateral panel 31 in an angular relation, generally perpendicular to, the main body 21, so as to separate the main body 21 from the perineal area. This expanded portion 34 may be present on one or both sides of the lateral panels 31, may extend completely to the fold 25, and may be formed from the same material as the lateral panels 31 or may comprise material, such as foam or other type padding materials, adjoined to the lateral panels 31.

To increase the ventilation effects of the device, perforations 91 may be located in the main body 21. An adhesive strip 92, of the type generally known and used with panty liners or sanitary napkins, may be positioned on the outer surface 23 of main body 21 for adhesively attaching the device to clothing to prevent movement of the device during use. Because the lateral panels 31 create a non-contact zone of approximately one inch between the inner surface 22 of the main body 21 and the perineal area, there is sufficient room if desired to adhesively attach a thin panty liner or absorbent pad to the inner surface 22 to absorb fluids while maintaining a separation zone between the absorbent pad and tile perineal area.

It is understood that obvious substitutions and equivalents may be known to those skilled in the art, and the examples set forth above are by way of illustration in regard to defining the invention should not be considered as limiting. The true scope and definition of the invention is to be as set forth in the following claims.

I claim:

1. A shield for use in the perineal area, the device comprising a main body and two lateral panels composed of a relatively rigid but flexible material, said main body having an inner surface, an outer surface and two opposing longitudinal edges, said two lateral panels being each connected to one of said longitudinal edges along a folding junction, each said folding junction being shorter than each said longitudinal edge, each of said two lateral panels having an arcuate outer edge which conforms to the perineal area when said device is worn, each said lateral panel having an expanded portion adjacent each said arcuate outer edge of greater thickness than said lateral panel and said main body, said expanded portions securing said lateral panels in proper position when said device is worn, where said device is relatively planar when said lateral panels are in the non-folded position, and whereby said lateral panels when folded in angular relation to said main body provide sufficient rigidity to separate and maintain said inner surface of said main body a distance away from the perineal area when said device is worn.

2. The device of claim 1, where said lateral panels each have curved panel ends, whereby said main body flexes longitudinally and contacts said curved panel ends when worn.

3. The device of claim 1, where each said expanded portion is padded.

4. The device of claim 1, where said main body is generally rectangular.

5. The device of claim 1, where said main body is generally bi-concave.

6. The device of claim 1, where said main body further comprises perforations.

7. The device of claim 1, further comprising an adhesive strip attached to said outer surface of said main body.

8. The device of claim 1, where said main body is composed of an absorbent material.

9. The device of claim 1, where said main body is longer than said lateral panels, such that said main body flexes longitudinally when said device is worn.

10. The device of claim 9, where said lateral panels have curved panel ends, whereby said main body when flexed longitudinally contacts said curved panel ends.

11. The device of claim 1, where said lateral panels are not centered along said longitudinal edges.

12. The device of claim 9, where said lateral panels are not centered along said longitudinal edges.

* * * * *